United States Patent [19]
Adams et al.

[11] Patent Number: 5,325,848
[45] Date of Patent: Jul. 5, 1994

[54] ENDOSCOPIC TISSUE MANIPULATOR WITH EXPANDABLE FRAME

[75] Inventors: Ronald D. Adams, Wyoming; Randy J. Embertson, Cincinnati, both of Ohio; M. Joshua Tolkoff, Brookline, Mass.; Robert C. Allman, Wakefield, Mass.; Fernando A. de Toledo, Concord, Mass.

[73] Assignee: Ethicon, Inc., Somerville, N.J.

[21] Appl. No.: 943,096

[22] Filed: Sep. 10, 1992

[51] Int. Cl.$^5$ ............................................. A61B 17/02
[52] U.S. Cl. ................................. 128/20; 606/198
[58] Field of Search ............ 606/191, 198, 108, 113, 606/159, 127; 128/20

[56] References Cited

U.S. PATENT DOCUMENTS

| | | | |
|---|---|---|---|
| 1,878,671 | 9/1932 | Cantor | 606/191 |
| 2,655,154 | 10/1953 | Richter | 606/159 |
| 3,448,741 | 6/1969 | Dennis et al. | 606/159 |
| 3,495,586 | 2/1970 | Regenbogen | 606/198 |
| 3,557,794 | 1/1971 | Van Patten | 606/198 |
| 4,590,938 | 5/1986 | Segura et al. | 606/127 |
| 4,654,028 | 3/1987 | Suma | 604/106 |
| 4,655,219 | 4/1987 | Petruzzi | 128/6 |
| 4,705,041 | 11/1987 | Kim | 606/108 |
| 5,152,771 | 10/1992 | Sabbaghian et al. | 606/198 |
| 5,195,505 | 3/1993 | Josefsen | 606/198 |
| 5,199,419 | 4/1993 | Remiszewski et al. | 606/198 |

FOREIGN PATENT DOCUMENTS

415039  5/1947  Italy ................................. 606/198

Primary Examiner—Tamara L. Graysay

[57] ABSTRACT

A tissue manipulator is provided which is insertable through an endoscopic tube to enable a surgeon to manipulate tissue inside a body cavity. The endoscopic tissue manipulator includes an expandable tissue manipulating frame adapted to expand transversely through a longitudinal slot in a support tube to provide a spatula-shaped platform which can be manipulated by rotation of the support tube about its longitudinal axis to engage and displace large body organs away from a desired surgical site in a body cavity. The frame consists of a plurality of flexible frame members or wires adapted to flex laterally outward through the longitudinal slot in the support tube into a bow-shaped configuration overlapping the other frame members or wires of the spatula-shaped platform. The instrument can be provided with a single tissue manipulating frame or a pair of frames which are expandable through separate longitudinal slots in the support tube to provide a pair of spatula-shaped platforms to engage the tissue. The pair of frames of the dual frame embodiment may be actuated together or independently.

32 Claims, 8 Drawing Sheets

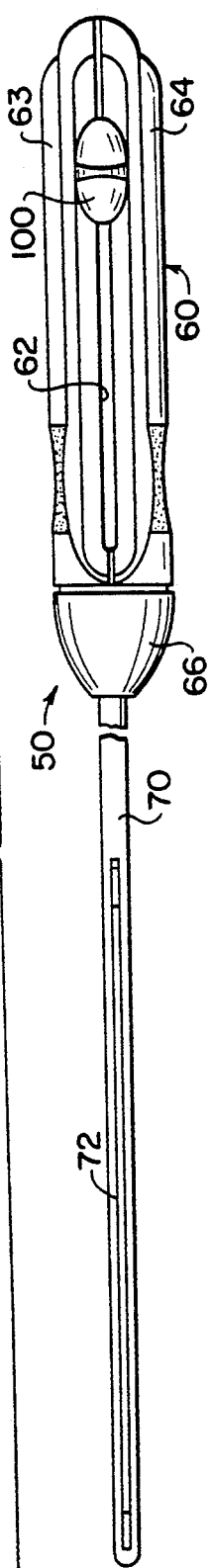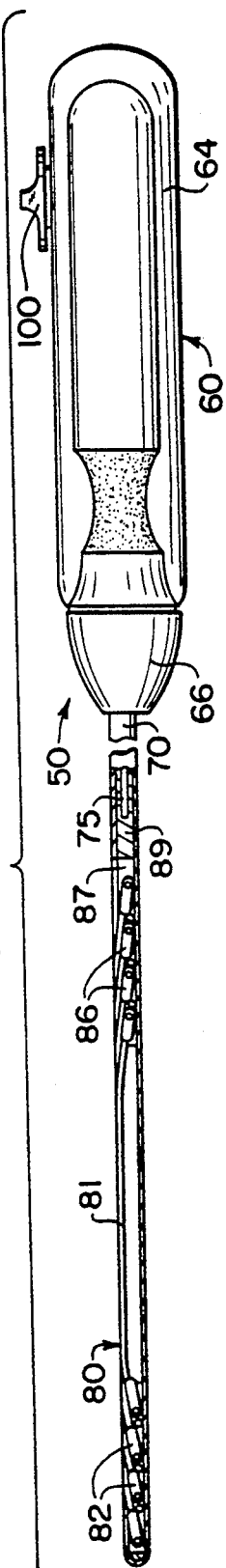

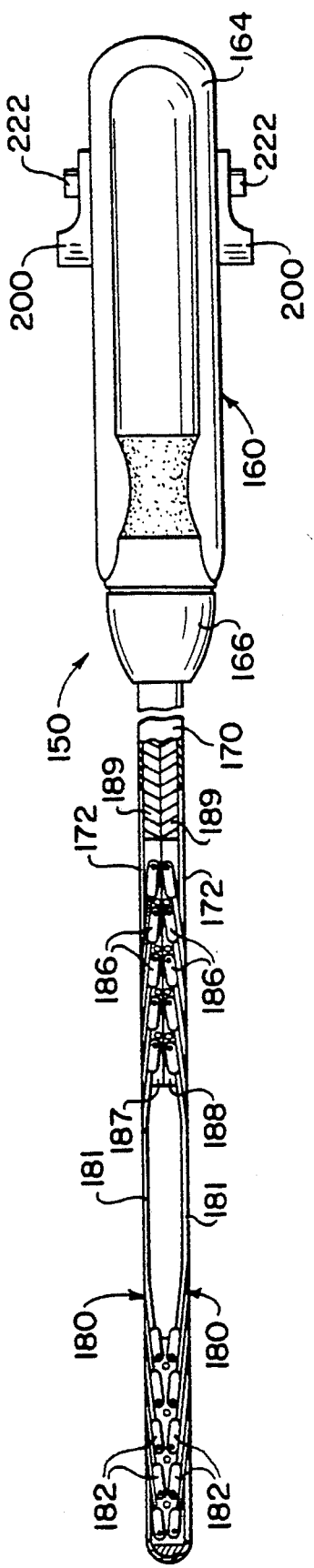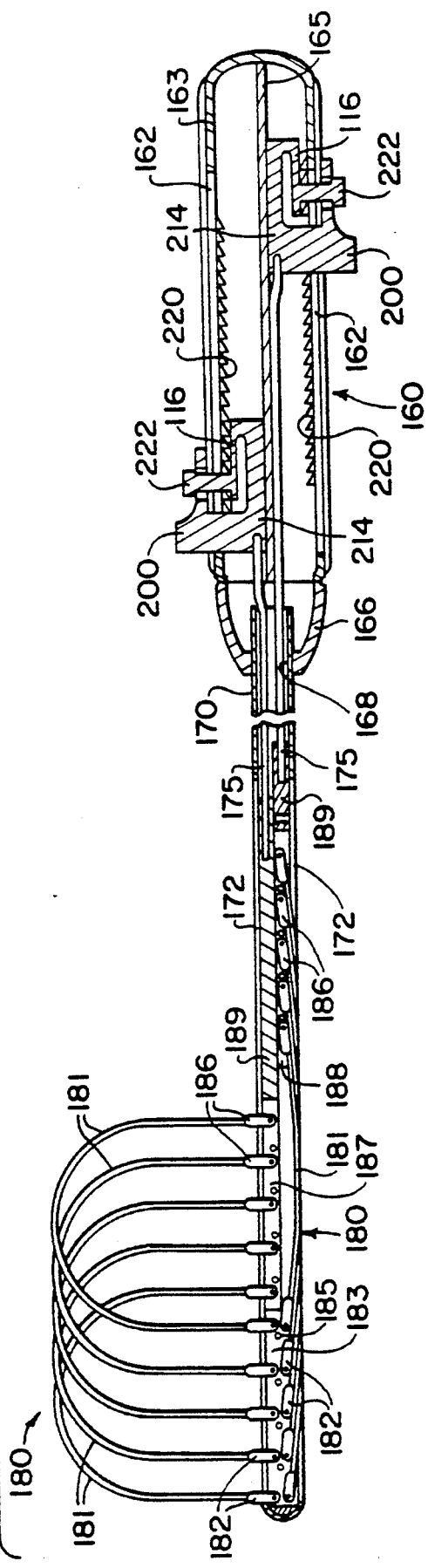
FIG. 11
FIG. 12

FIG. 16
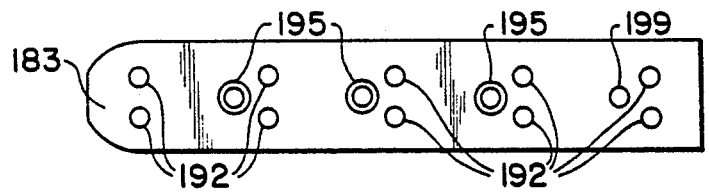
FIG. 18     FIG. 17
 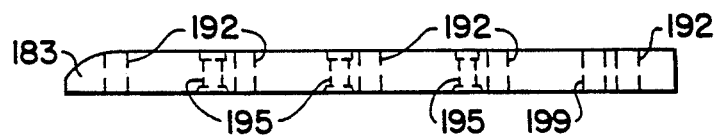
FIG. 19
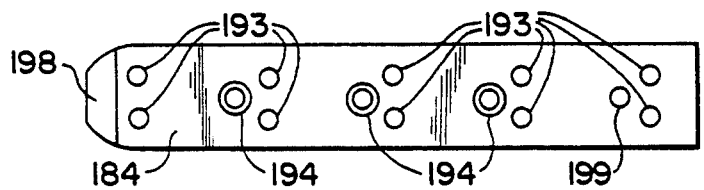
FIG. 21     FIG. 20
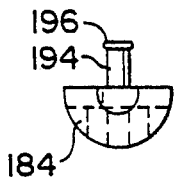 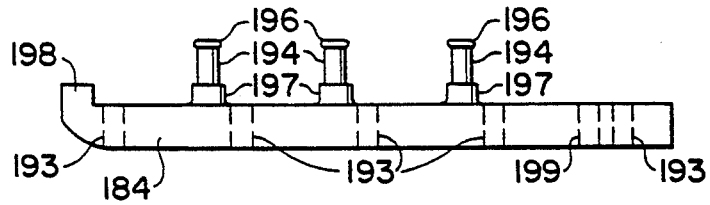
FIG. 22
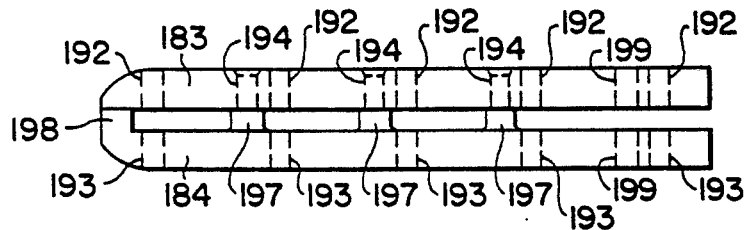
FIG. 23     FIG. 24
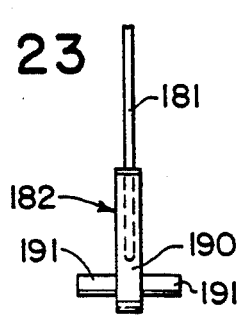 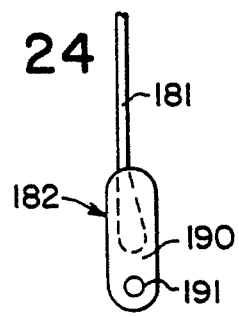

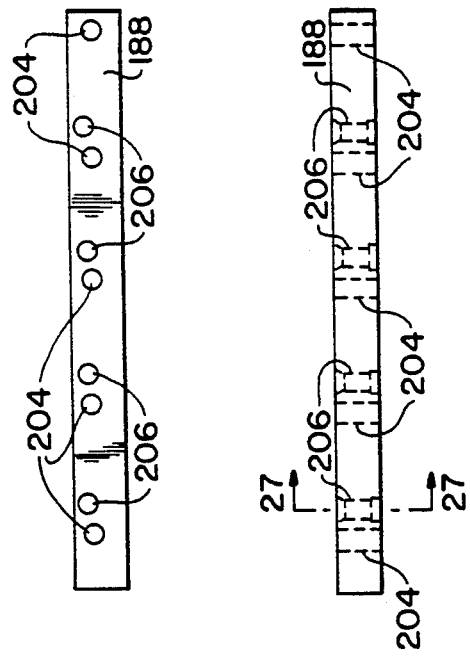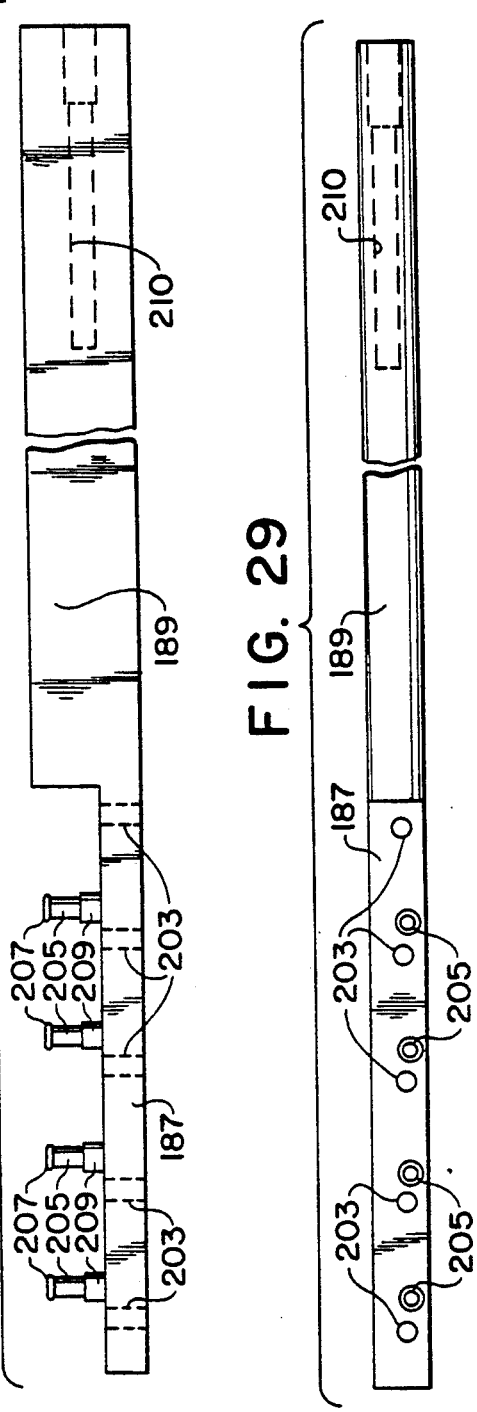

ENDOSCOPIC TISSUE MANIPULATOR WITH EXPANDABLE FRAME

FIELD OF THE INVENTION

The present invention relates to a tissue manipulator adapted for manipulating tissue in a human body and, more particularly, to an endoscopic tissue manipulator with an expandable frame which is insertable through a trocar sleeve to enable a surgeon to manipulate tissue inside a body cavity. Also, the invention concerns an endoscopic tissue manipulator which is particularly suitable for use by a surgeon to displace large body organs, e.g., the liver, lungs, stomach or intestines, to enable surgery to be performed at a desired surgical site.

BACKGROUND OF THE INVENTION AND PRIOR ART

Endoscopic procedures have been developed for observing and treating internal body organs. Such procedures involve the insertion of an endoscope into a natural body orifice or through an incision in the body which allows a surgeon to observe and treat tissue inside a body cavity. Flexible endoscopes have been developed for insertion into natural body orifices, e.g., through the mouth or into the rectum. Also, rigid endoscopes have been developed for insertion into the abdominal cavity or the thoracic cavity through incisions at the surface of the body. Typically, a trocar is inserted into a trocar sleeve or tube to facilitate the insertion of the trocar sleeve through an incision and its penetration through internal body tissue. After the trocar sleeve is positioned at a desired surgical site, the trocar is removed from the trocar sleeve to allow another instrument such as an endoscope or forceps to be inserted into the trocar sleeve and advanced into contact with the tissue at the surgical site. The observation and treatment of the tissue can be made difficult by large body organs, e.g., the liver, lungs or intestines, which must be displaced to provide access to the surgical site.

In the prior art, several types of instruments are known for manipulating internal body tissue. For example, U.S. Pat. No. 4,909,789 discloses observation assisting forceps including a set of expandable wires mounted on a shaft which is normally retracted into a sheath. When the shaft is advanced, the wires project out of the sheath and expand into a fan-shaped configuration in the same plane. The expanded wires can be used to set aside internal organs obstructing the observation with an abdominal cavity endoscope. The wires are provided at the tips with spherical members which prevent the organs from being hurt.

U.S. Pat. No. 4,654,028 discloses an incision opening expansion holder including a plurality of wires at the end of an inner tube which are three dimensionally expanded when projecting out of an outer tube to expand an incision of a blood vessel graft for purposes of inosculation. U.S. Pat. No. 4,705,041 discloses a tissue dilator comprising a catheter which supports an expandable member, e.g., a balloon or a scissor-like member. U.S. Pat. No. 1,878,671 discloses a dilator for opening a body cavity including an ovate head mounted on a wire received in a tube which is inserted into the body cavity.

U.S. Pat. No. 4,655,219 discloses a tissue grasping accessory including a plurality of flexible grasping arms for use with an endoscopic instrument to grasp a tissue specimen. U.S. Pat. No. 4,590,938 discloses a device for removal of kidney stones through the working channel of an endoscope including a basket comprising four outwardly bowed, generally flat spring arms which are expandable into a bulbous shape and collapsed when retracted into a sheath. The relatively broad, flat surfaces of the spring strips deflect the kidney tissue surrounding the stone while the distally enlarged volume of the basket allows the surgeon to dislodge and capture the stone.

None of the above described devices are particularly suited for use in manipulating large body organs, e.g., the liver, lungs or intestines, away from a desired surgical site. Moreover, it appears that several of the devices may have a tendency to damage the tissue if attempted to be used to displace large body organs.

Accordingly, it is an object of the present invention to provide a tissue manipulator which is adapted to safely manipulate internal body tissue.

Another object of the invention is to provide a tissue manipulator for insertion through an endoscopic device to manipulate tissue such as large body organs in a body cavity.

It is also an object of the invention to provide an endoscopic tissue manipulator which is suitable for insertion through a trocar sleeve into a body cavity for displacing or retaining large body organs, e.g., the liver, lungs or intestines, away from a desired surgical site.

It is another object of the invention to provide an endoscopic tissue manipulator including an expandable tissue manipulating frame adapted to expand laterally outward through a longitudinal slot in a support tube to provide a spatula-shaped platform which can be manipulated by rotation of the support tube about its longitudinal axis to engage and displace large body organs away from a desired surgical site in a body cavity.

SUMMARY OF THE INVENTION

The present invention achieves an improved tissue manipulator which is adapted for insertion through an endoscopic tube or cannula into a body cavity to manipulate internal body tissue therein. The tissue manipulator includes an expandable frame which is particularly suitable for engaging large body organs, e.g., the liver, lungs or intestines, without risk of injury to such organs. The expandable frame allows the large body organs to be displaced away from a desired surgical site and to be constrained in a position which does not obstruct access to the desired surgical site. The frame consists of a plurality of flexible frame members or wires adapted to flex transversely through a longitudinal slot in a support tube into a bow-shaped configuration overlapping the other frame members or wires to provide a spatula-shaped platform for manipulating the tissue. The instrument can be provided with a single tissue manipulating frame or a pair of tissue manipulating frames which are expandable laterally through separate longitudinal slots in the support tube to provide a pair of spatula-shaped platforms to engage the tissue.

In accordance with the invention, the endoscopic tissue manipulator comprises a handle, a support tube extending from the handle and including an elongated slot formed therein, an expandable frame mounted within the support tube adjacent to the slot, and means for expanding the frame transversely from the support tube through the slot to provide a spatula-shaped platform for manipulating tissue. The frame comprises one or more elongated flexible frame members, each frame member being adapted to flex laterally relative to the support tube. Each frame member is adapted to bend into a bow-shaped configuration extending laterally from the slot and overlapping the other frame members of the platform. The frame members are adapted to form a substantially planar platform located in the same plane with the longitudinal axis of the support tube.

In a preferred embodiment of the tissue manipulating frame, the frame members comprise a series of wires adapted to expand laterally outward from the support tube into a substantially planar configuration for engaging the tissue. The wires are staggered along the support tube and arranged in an overlapping relationship with respect to one another. The wires are expandable from a collapsed configuration within the support tube to an expanded configuration projecting laterally from the slot in the support tube for manipulation of the tissue.

Another aspect of the invention relates to an endoscopic tissue manipulator including a pair of expandable tissue manipulating frames which are actuated independently of each other. The tissue manipulator comprises a handle, a support tube extending from the handle and including a pair of elongated slots formed therein on opposite sides of the support tube, a pair of expandable frames mounted within the support tube, each of the expandable frames being located adjacent to one of the slots, and means for selectively expanding the frames transversely from the support tube through the slots to provide spatula-shaped platforms for manipulating tissue. Each frame comprises one or more elongated flexible frame members, each frame member being adapted to flex laterally relative to the support tube. Each frame member is adapted to bend into a bow-shaped configuration extending laterally from one of the slots and overlapping the other frame members of one of the platforms. The frame members are adapted to form a substantially planar platform located in the same plane with the longitudinal axis of the support tube.

In the dual frame embodiment of the tissue manipulator, the frame members of each frame comprise a series of wires adapted to expand laterally outward from the support tube into a substantially planar configuration for engaging the tissue. The wires of each frame are staggered along the support tube and arranged in an overlapping relationship with respect to one another. The wires of each frame are expandable from a collapsed configuration within the support tube to an expanded configuration projecting laterally from one of the slots in the support tube to provide a substantially planar platform for manipulation of the tissue.

In accordance with another aspect of the invention, the endoscopic tissue manipulator comprises a handle, an elongated hollow support tube extending from the handle and defining a longitudinal axis, the support tube having a longitudinal slot formed therein adjacent to its distal end, an actuator member mounted for longitudinal movement relative to the support tube, an expandable frame comprising a set of elongated frame members, each of the frame members being connected at its opposite ends to the support tube and to the actuator member, and the frame members being adapted to flex transversely relative to the longitudinal axis through the slot in the support tube by movement of the actuator member relative to the support tube to provide a spatula-shaped platform for manipulating tissue. Each of the frame members is adapted to bend into a bow-shaped configuration extending laterally from the slot and overlapping the other frame members of the platform.

Preferably, the frame members of the tissue manipulator are adapted to expand from a collapsed configuration within the support tube to an expanded configuration projecting laterally from the slot in the support tube. A manually operable actuator slide is mounted on the handle and connected to the actuator member for moving the actuator member longitudinally relative to the support tube to expand and collapse the frame members. A ratchet mechanism is provided on the handle for releaseably engaging the actuator slide to retain the frame members in an expanded or collapsed configuration. A manually operable release button is provided on the actuator slide for disengaging the actuator slide from the ratchet mechanism to allow the frame members to return to the collapsed configuration.

In the preferred embodiment, the frame members of the endoscopic tissue manipulator comprise a series of wires adapted to expand laterally outward from the support tube into a substantially planar configuration for engaging the tissue. The wires are staggered along the support tube and arranged in an overlapping relationship with respect to one another. The frame includes means for pivotally connecting the distal end of each wire to the support tube and means for pivotally connecting the proximal end of each wire to the actuator member.

The dual frame embodiment of the tissue manipulator is provided with a pair of expandable tissue manipulating frames each comprising a set of elongated flexible frame members which are actuated independently and are expanded transversely through one of the longitudinal slots on opposite sides of the support tube. A pair of actuator members is mounted for longitudinal movement relative to the support tube for actuating each of the expandable tissue manipulating frames. A pair of manually operable actuator slides is mounted on the handle and each slide is connected to one of the actuator members for moving the actuator member relative to the support tube to expand and collapse one set of the frame members. A ratchet mechanism is provided on the handle for releaseably engaging each of the actuator slides to retain each set of frame members in an expanded or collapsed configuration. A manually operable release button is provided on each actuator slide for disengaging the actuator slide from its ratchet mechanism to allow each set of frame members to return to the collapsed configuration.

BRIEF DESCRIPTION OF THE DRAWINGS

The foregoing and other objects, aspects and advantages will be better understood from the following detailed description of the preferred embodiments of the invention with reference to the drawings, in which:

FIG. 2 is a partially cutaway top view of the tissue manipulator of FIG. 1;

FIG. 3 is a partially cutaway side view of the tissue manipulator of FIG. 1 with its tissue manipulating frame collapsed;

FIG. 4 is a partially cutaway side view of the tissue manipulator of FIG. 1 with its tissue manipulating frame expanded;

FIG. 11 is a partially cutaway side view of another embodiment of a tissue manipulator having a pair of tissue manipulating frames;

FIG. 12 is a partially cutaway side view of the tissue manipulator of FIG. 11 with one of its frames expanded and the other collapsed;

FIG. 16 is a side view showing a portion of a frame support member of FIG. 15;

FIG. 17 is a top view of the frame support member of FIG. 16;

FIG. 18 is an end view of the frame support member of FIG. 17;

FIG. 19 tissues a side view of another portion of the frame support member of FIG. 15;

FIG. 20 is a top view of the frame support member of FIG. 19;

FIG. 21 tissues an end view of the frame support member of FIG. 20;

FIG. 22 is a top view showing the frame support members assembled together;

FIGS. 23 and 24 show a pivot anchor forming part of the tissue manipulator of FIG. 15;

FIG. 25 is a side view showing a portion of a frame actuator member of FIG. 15;

FIG. 26 is a bottom view of the frame actuator member of FIG. 25;

FIG. 27 is a vertical section the frame actuator member along line 27—27 of FIG. 26;

FIG. 28 is a side view of another portion of the frame actuator member of FIG. 15;

FIG. 29 is a bottom view of the frame actuator member of FIG. 28; and

FIG. 30 is an end view of the frame actuator member of FIG. 29.

DETAILED DESCRIPTION OF PREFERRED EMBODIMENTS

Figure 1:
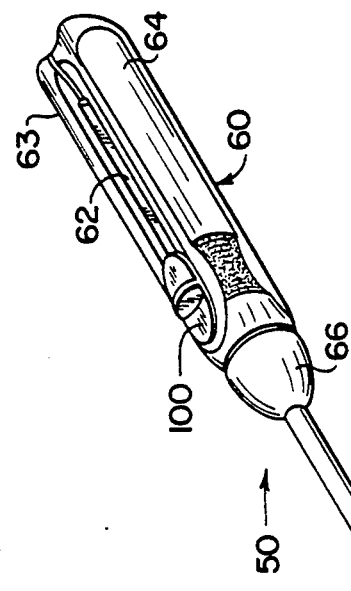
FIG. 1 is a perspective view of an endoscopic tissue manipulator constructed in accordance with this invention.
Figure 8:
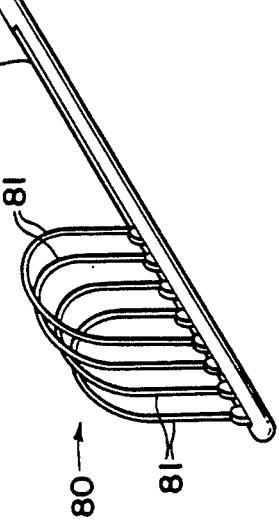
FIG. 8 is a front view of an actuator slide on the handle assembly of FIG. 6.
Figure 9:
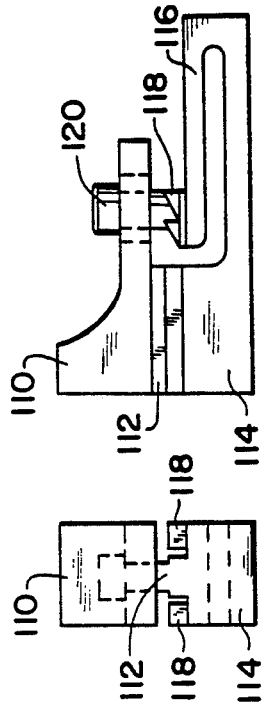
FIG. 9 is a side view of the actuator slide of FIG. 6.
Figure 10:
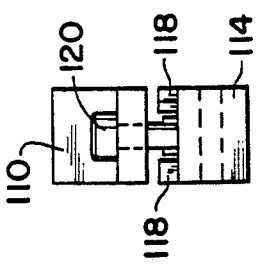
FIG. 10 is a rear view of the actuator slide of FIG. 6.
Figure 6:
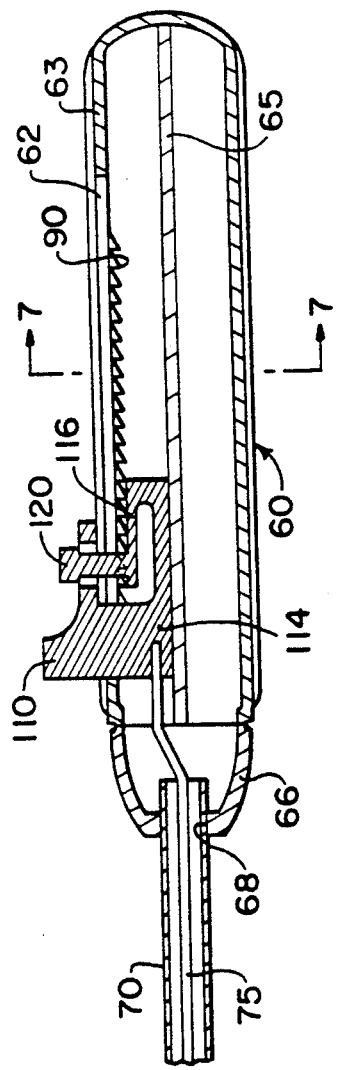
FIG. 6 is an enlarged partially cutaway side view showing another embodiment of the handle assembly of the tissue manipulator of FIG. 1.

Referring to FIG. 1, the present invention is embodied in an endoscopic tissue manipulator, generally 50, which is insertable through a trocar tube or cannula to enable a surgeon to manipulate tissue inside a body cavity. The endoscopic tissue manipulator 50 is particularly suitable for use by a surgeon to displace large body organs, e.g., the liver, stomach or intestines, to enable surgery to be performed at a desired surgical site. The tissue manipulator 50 includes a proximal handle assembly 60 with an elongated support tube 70 extending therefrom. The support tube 70 includes an elongated slot 72 formed adjacent to its distal end. An expandable frame 80 comprising a plurality of elongated flexible frame members 81 is mounted within the support tube 70 adjacent to the slot 72. The frame members 81 are expandable laterally outward through the slot 72, after insertion of the tissue manipulator 50 inside the body, to provide a spatula-shaped platform for manipulating tissue in a body cavity. An actuator slide 100 is slidably mounted for movement in an elongated slot 62 at the top of the handle assembly 60 for expanding the frame 80 into the desired configuration for manipulating tissue. The expanded frame 80 has a substantially planar configuration and can be used in spatula-like fashion, by using the support tube 70 as a lever or by rotating the support tube 70 about its longitudinal axis, to manipulate tissue, e.g., large body organs, inside the body.

As shown in FIGS. 1-4, the handle assembly 60 includes a pair of handle sections 63 and 64 which fit together to provide a hollow elongated handle. A conical nose piece 66 is mounted at the front end of the handle sections 63 and 64. The nose piece 66 has a central opening 68 in which the support tube 70 is mounted. The actuator slide 100 is slidably mounted for movement along the slot 62 formed between the handle sections 63 and 64 for expanding the frame 80 into a desired configuration for manipulating tissue. The actuator slide 100 is movable between a retracted position (FIG. 3) in which the frame 80 is collapsed and an advanced position (FIG. 4) in which the frame 80 is expanded into a spatula-shaped platform.

FIGS. 1-5 show a single-sided embodiment of the tissue manipulator 50 in which the support tube 70 has, for example, an outer diameter of 5 mm. It will be understood, however, by persons skilled in the art, that other smaller and larger diameters can be used for the support tube 70. A single longitudinal slot 72 extends along the top of the support tube 70 and a single actuator slide 100 is mounted on the handle assembly 60 for expanding and collapsing the tissue manipulating frame 80 through the slot 72.

Figure 5:
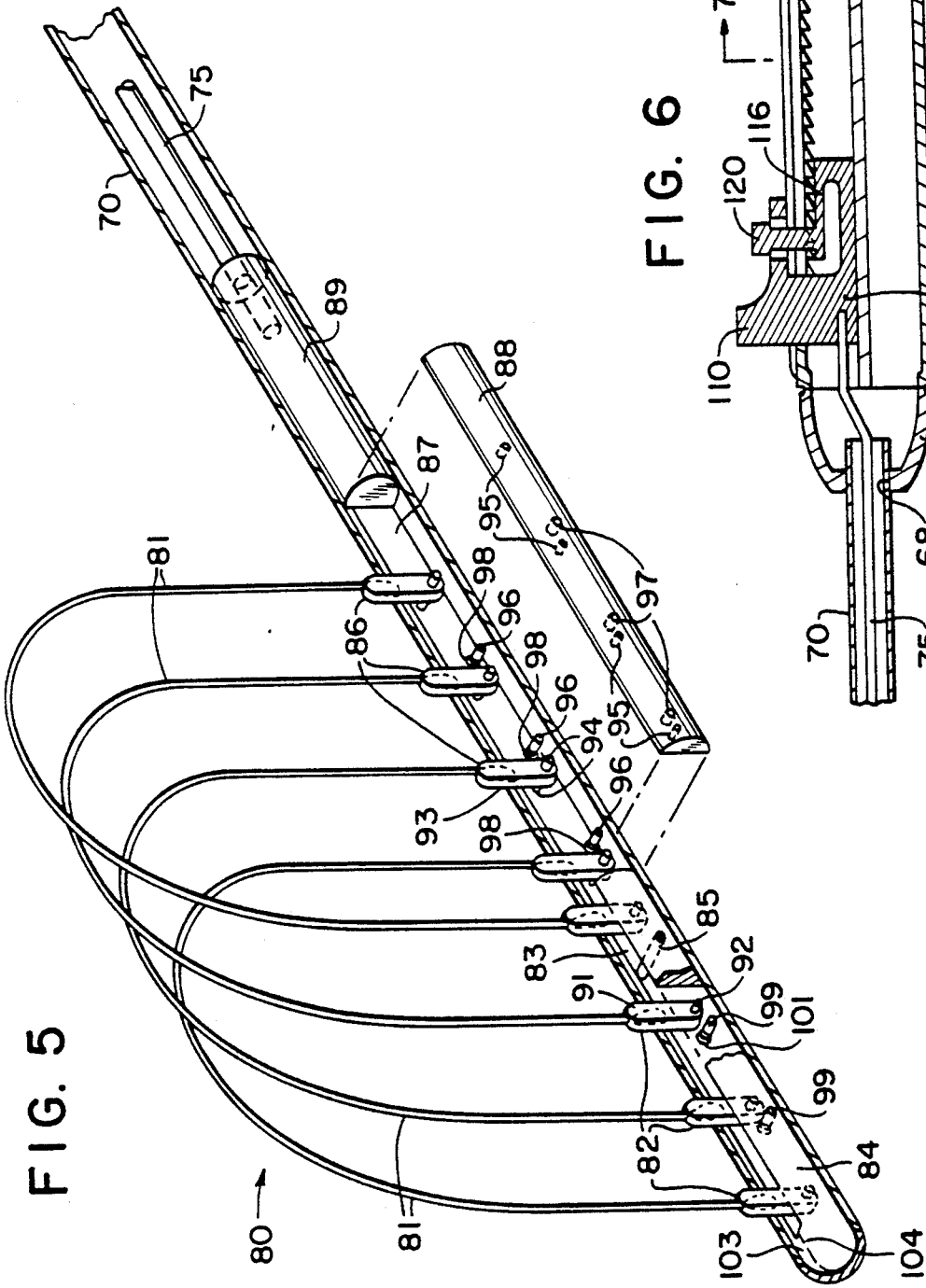
FIG. 5 is a partially cutaway perspective view of the tissue manipulator of FIG. 1 showing the components of the tissue manipulating frame.

As shown in FIG. 5, the expandable frame or platform 80 consists of a plurality of elongated flexible frame members 81, each of which is adapted to bend into a bow-shaped configuration extending laterally outward through the slot 72 in the support tube 70 in an overlapping relationship with the other frame members 81 of the platform 80. Preferably, each frame member 81 consists of an elongated stainless steel wire.

In the embodiment of FIGS. 1-5, the tissue manipulating frame 80 consists of four elongated flexible frame members or wires 81 which are substantially equal in length and are staggered longitudinally along the support tube 70 relative to one another. Each wire 81 is secured at its distal end to an anchor 82 which, in turn, is pivotally mounted on a pair of semi-cylindrical clam shell members 83 and 84 coupled to the distal end of the support tube 70. The distal clam shell members 83 and 84 together provide a fixed platform support member which is secured to the distal end of support tube 70 by a transverse retainer pin 85. Also, the retainer pin 85 is used to secure the opposite sides of the support tube 70 together in the region of the slot 72. In addition, each wire 81 is secured at its proximal end to an anchor 86 which, in turn, is pivotally connected to a semi-cylindrical clam shell member 87 which mates with a semi-cylindrical clam shell section 88. The clam shell member 87 and its mating clam shell section 88 together provide a slidable platform actuator member mounted for longitudinal movement within the support tube 70. The clam shell member 88 has an elongated cylindrical extension 89 connected by an actuator rod 75 to the actuator slide 100.

As shown in FIG. 5, each distal anchor 82 has a narrow wire receiving body 91 provided with a pair of pivot pins 92 extending laterally from opposite sides of the body 91. The distal end of the wire 81 is flattened and embedded in the wire receiving body 91. The flattened distal end of the wire 81 is serrated to firmly grip the body 91 of the anchor 82. The pivot pins 92 are pivotally received in a series of uniformly spaced holes formed in the distal clam shell members 83 and 84.

The proximal anchors 86 are substantially identical in construction to the distal anchors 82. Each anchor 86 has a narrow wire receiving body 93 provided with a pair of pivot pins 94 extending laterally from opposite sides of the body 93. The proximal end of the wire 81 is flattened and embedded in the wire receiving body 93. The flattened proximal end of the wire 81 is serrated to firmly grip the body 93 of the anchor 86. The pivot pins 94 are pivotally received in a series of uniformly spaced holes 95 formed in the proximal clam shell member 87 and in its mating clam shell section 88.

Referring to FIG. 5, the proximal clam shell member 87 has a series of longitudinally spaced fastener posts 96 which are adapted to be snap fit into a corresponding set of longitudinally spaced bores 97 formed in the mating clam shell section 88. The base of each fastener post 96 has an enlarged pedestal 98 which serves as a spacer to maintain a sufficient space between the proximal clam shell member 87 and the mating clam shell section 88 to receive the anchors 86 therebetween. Similarly, the distal clam shell member 83 includes a pair of longitudinally spaced fastener posts 99 which are adapted to be snap fit into a pair of longitudinally spaced bores formed in the other distal clam shell member 84. Each fastener post 99 includes an enlarged pedestal 101. The fastener posts 96 and 99 of the single-sided instrument (FIG. 5) are substantially identical in structure to those of the double-sided instrument (FIG. 15) described in more detail below. A set of laterally projecting ledges 103 and 104 is provided at the front ends of the distal clam shell members 83 and 84, respectively. When the distal clam shell members 83 and 84 are assembled, the pedestals 101 and the ledges 103 and 104 serve as spacers to maintain a sufficient distance between the clam shell members 83 and 84 to receive the anchors 82. Alternatively, only one laterally projecting ledge can be formed at the front of either of the clam shell members 83 and 84 to maintain the desired spacing therebetween.

Figure 7:
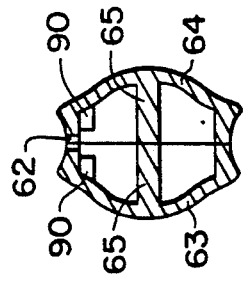
FIG. 7 is a vertical section of the handle assembly taken along line 7—7 of FIG. 6.

As shown in FIG. 4, the acutator slide 100 has a narrow elongated neck 106 which is slidably received in the slot 62 at the top of the handle assembly 60. The neck 106 of the actuator 100 is connected by a resilient hinge 107 to the front of an elongated base 108 which is slidably supported by a horizontal partition 65 extending along the longitudinal axis of the handle assembly 60. The proximal end of the acutator rod 75 is also secured to the front of the base 108. The actuator slide 100 includes one or more pawls 109 which are normally biased by the resilient hinge 107 into engagement with a ratchet 90 formed inside of each of the handle sections 63 and 64 to retain the actuator slide 100 in a selected position on the handle assembly 60. The ratchets 90 (FIG. 7) extend longitudinally along opposite sides of the slot 62. The pawls 109 and the ratchets 90 provide a ratchet mechanism for retaining the frame members or wires 81 in an outwardly expanded or an inwardly collapsed configuration.

Preferably, except for the wires 81, the other frame components including the anchors 82 and 86, the distal clam shell members 83 and 84, and the proximal clam shell member 87 and its mating clam shell section 88 are made of plastic material. The support tube 70 and actuator rod 75 consist of stainless steel. The components of the handle assembly 60 and the actuator slide 100 are made of plastic material.

In the operation of the single-sided embodiment of FIGS. 1-5, the endoscopic tissue manipulator 50 is inserted into a body cavity through a trocar tube or cannula installed in the body wall. An endoscope may be inserted into the body cavity through a separate trocar tube or cannula for observation of the surgical site. The tissue manipulator 50 is advanced toward the surgical site by pushing on the handle assembly 60 to slide the support tube 70 through the trocar tube or cannula. The support tube 70 is advanced until its distal end is positioned adjacent to the desired surgical site.

When it is desired to expand the platform 80, the surgeon engages the actuator slide 100 with his thumb while holding the handle assembly 60 with the remaining fingers in one hand. By advancing the actuator slide 100 distally, as shown in FIG. 4, the actuator rod 75 is advanced in the distal direction to slide the proximal clam shell member 87 and its mating clam shell section 88 toward the distal clam shell members 83 and 84. As a result, the anchors 82 and 86 are pivoted outwardly through the slot 72 and the frame members or wires 81 are expanded laterally outward into a bow-shaped configuration. The bow-shaped wires 81 provide a substantially planar platform 80 located in the same plane with the longitudinal axis of the support tube 70. Each bow-shaped wire 81 overlaps the remaining bow-shaped wires of the platform 80. With the platform 80 fully expanded, the proximal and distal ends of the wires 81 are substantially perpendicular to the support rod 70. The actuator slide 100 is maintained in its fully advanced position by the pawls 109 which engage the ratchets 90. As a result, the frame members or wires 81 are retained in the fully expanded configuration. The platform 80 can be partially expanded, if desired, by moving the actuator slide 100 to an intermediate position on the handle assembly 60.

After the platform 80 is expanded to the desired size and shape, the tissue manipulator can be used in a spatula-like manner to engage a large body organ, e.g., the liver, stomach or intestines, adjacent to the desired surgical site in the body cavity. The expanded platform 80 provides a flat tissue manipulating face on each of its opposite sides. The spatula-shaped platform 80 is oriented with one of its flat faces engaging the large body organ. Then, by manipulating the handle assembly 60 to rotate the support tube 70 about its longitudinal axis, the planar platform 80 can be urged against the large body organ, in a manner similar to the use of a spatula, to displace or retain the large body organ in a desired position away from the surgical site.

When it is desired to remove the tissue manipulator 50 from the trocar tube or cannula, the platform 80 is collapsed by depressing and sliding the actuator slide 100 rearwardly on the handle assembly 60. As a result, the actuator rod 75 is retracted to slide the proximal clam shell member 87 and its mating clam shell section 88 rearwardly away from the distal clam shell members 83 and 84. The bow-shaped wires 81 are retracted into the slot 72 and the platform 80 is returned to its collapsed configuration (FIG. 2). Then, by grasping and pulling the handle assembly 60, the tissue manipulator 50 is removed from the trocar tube or cannula.

Referring to FIGS. 6-10, an alternative embodiment of the handle assembly 60 includes an actuator slide 110 having a narrow elongated neck 112 which is slidably received in the longitudinal slot 62 in the handle assembly 60. The neck 112 is connected to the front of an elongated base 114 which is slidably supported by the horizontal partition 65 extending along the longitudinal axis of the handle assembly 60. The proximal end of the actuator rod 75 is also connected to the front of the base 114. A resilient hinge 116 is mounted at the rear of the base 114 and is provided with a set of pawls 118 which are normally biased by the resilient hinge 116 into engagement with the ratchets 90 on each of the handle sections 63 and 64 to retain the actuator slide 110 in a selected position on the handle assembly 60. The pawls 118 and the ratchets 90 provide a ratchet mechanism for retaining the frame members or wires 81 in an outwardly expanded configuration or an inwardly collapsed configuration. A manually operable release button 120 extends upwardly from the resilient hinge 116 through an opening in the actuator slide 110. The release button 120 is depressed to disengage the pawls 118 from the ratchet 90 to allow the frame members 81 to return to the collapsed configuration. As the release button 120 is depressed, the thumb of the surgeon also engages the actuator slide 110 to prevent the sudden collapse of the frame members 81 when the pawls 118 are disengaged from the ratchet 90.

FIGS. 11-15 show a double-sided embodiment of a tissue manipulator 150 having a handle assembly 160 and a hollow elongated support tube 170 with an outer diameter of 10 mm. It will be understood, however, by persons skilled in the art, that other smaller and larger diameters can be used for the support tube 170. The handle assembly 160 includes a pair of handle sections 163 and 164 which provide a hollow elongated handle. A conical nose piece 166 is mounted at the front end of the handle sections 163 and 164. The nose piece 166 has a central opening 168 in which the support tube 170 is mounted. A pair of longitudinal slots 172 extends along the top and bottom of the support tube 170 adjacent to its distal end. The tissue manipulator 150 includes upper and lower tissue manipulating frames 180 located adjacent to the slots 172. A pair of actuator slides 200 is slidably mounted in a pair of slots 162 formed in the handle assembly 160 for selectively expanding and collapsing the tissue manipulating frames 180 through the slots 172.

Figures 13, 14:
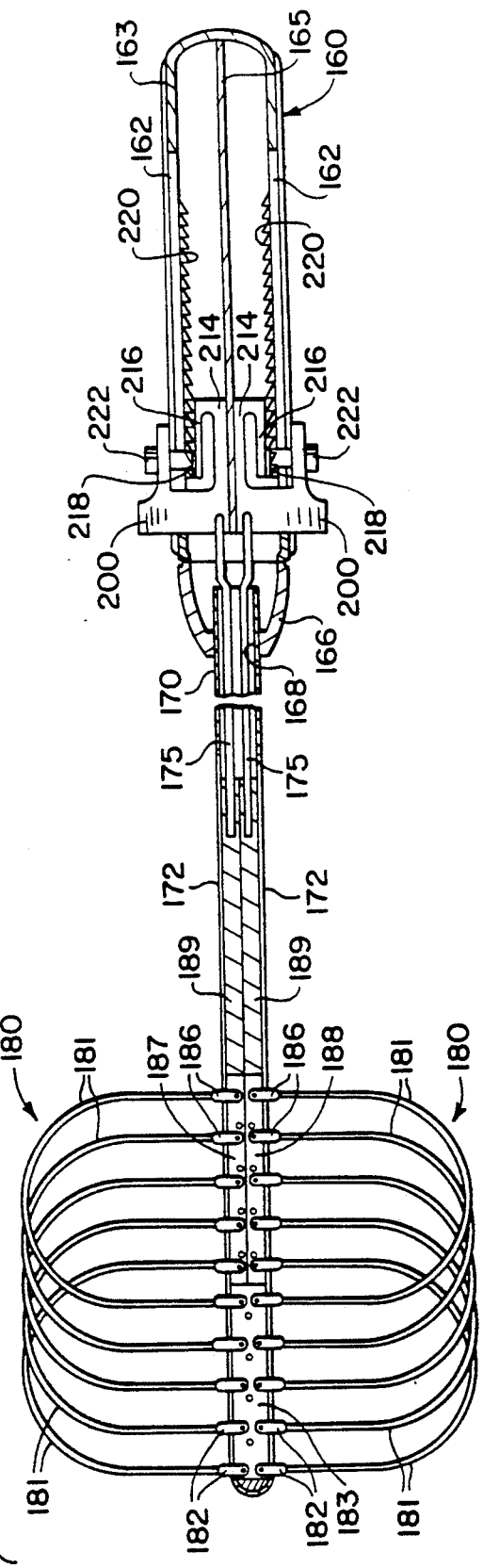
FIG. 13 is a partially cutaway side view of the tissue manipulator of FIG. 11 showing one of its frames fully expanded and the other partially expanded.
FIG. 14 is a partially cutaway side view of the tissue manipulator of FIG. 11 showing both of its frames expanded.

As shown in FIG. 13, each expandable frame or platform 180 includes a plurality of elongated flexible frame members 181, each of which is adapted to bend into a bow-shaped configuration extending laterally outward through one of the slots 172 in the support tube 170 in an overlapping relationship with the other frame members 181 of the platform 180. Preferably, each frame member 181 consists of an elongated stainless steel wire.

In the embodiment of FIGS. 11-15, each frame 180 consists of five elongated flexible frame members or wires 181 which are substantially equal in length and are staggered longitudinally along the support tube 170 relative to one another. Each wire 181 is secured at its distal end to an anchor 182 which, in turn, is pivotally mounted between a pair of semi-cylindrical clam shell members 183 and 184 coupled to the distal end of the support tube 170. The distal clam shell members 183 and 184 together provide a fixed platform support member which is secured to the distal end of the support tube 170 by a transverse retainer pin 185. Also, the retainer pin 185 is used to secure the opposite sides of the support tube 170 together in the region of the slots 172. In addition, each wire 181 is secured at its proximal end to an anchor 186 which, in turn, is pivotally connected to a semi-cylindrical clam shell member 187 which mates with a clam shell section 188. The elongated clam shell member 187 and its mating clam shell section 188 together provide a slidable platform actuator member mounted for longitudinal movement within the support tube 170. The clam shell member 188 has an elongated semi-cylindrical extension 189 connected by an actuator rod 175 to the actuator slide 200.

As shown in FIGS. 23 and 24, each anchor 182 has a narrow wire receiving body 190 provided with a pair of pivot pins 191 extending laterally from opposite sides of the body 190. The distal end of the wire 181 is flattened and embedded in the wire receiving body 190. The flattened distal end of the wire 181 is serrated to firmly grip the body 191 of the anchor 182.

Referring to FIGS. 16 and 19, the distal clam shell members 183 and 184 each include a series of holes 192 and 193, respectively, which are longitudinally spaced apart at equal intervals and receive the pivot pins 191 to pivotally mount the anchors 182 at the distal end of the support rod 170. Also, the distal clam shell member 184 includes a series of longitudinally spaced fastener posts 194 (FIG. 20) which are adapted to be snap fit into a corresponding set of longitudinally spaced bores 195 formed in the other distal clam shell member 183. Each fastener post 194 includes an outwardly projecting annular lip 196 at its free end to provide the snap fit of the fastener post 194 into the corresponding bore 195. As shown in FIG. 17, each bore 195 is slightly enlarged at its opposite ends to facilitate the entry of the fastener post 194 into the the bore 195 and to secure the annular lip 196 therein. Also, the base of each fastener post 194 includes an enlarged pedestal 197 (FIG. 20). A laterally projecting ledge 198 is provided at the front end of the distal clam shell member 184. As shown in FIG. 22, when the distal clam shell members 183 and 184 are assembled, the pedestals 197 and the ledge 198 serve as spacers to maintain a sufficient space between the clam shell members 183 and 184 to receive the anchors 182. An opening 199 is formed in each of the clam shell members 183 and 184 for receiving the transverse retainer pin 185.

Figure 15:
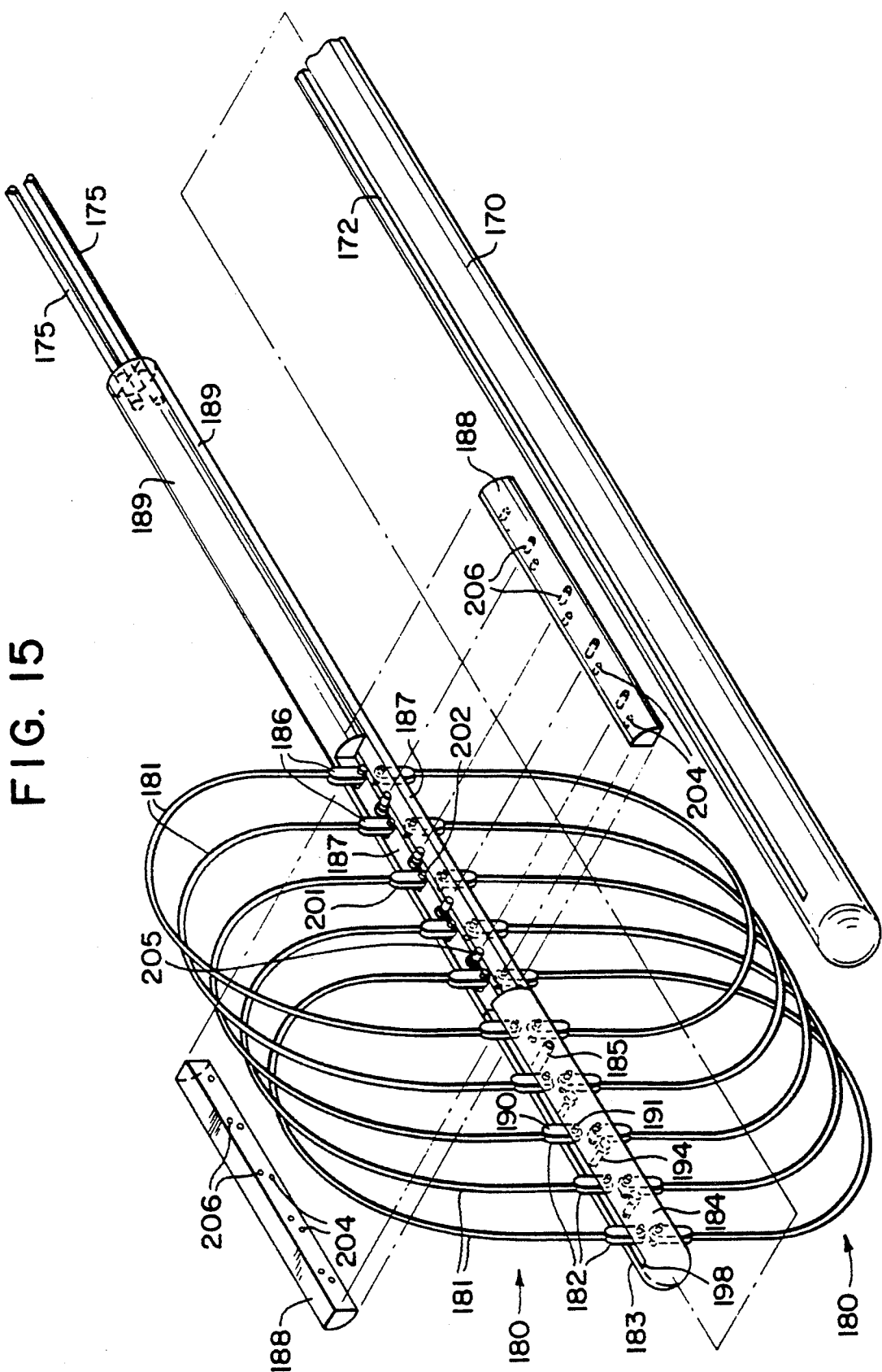
FIG. 15 is a partially cutaway perspective view of the tissue manipulator of FIG. 11 showing the components of the tissue manipulating frames.

Referring to FIG. 15, the proximal anchors 186 are substantially identical in construction to the distal anchors 182. Each anchor 186 has a narrow wire receiving body 201 provided with a pair of pivot pins 202 extending laterally from opposite sides of the body 201. The proximal end of the wire 181 is flattened and embedded in the wire receiving body 201. The flattened proximal end of the wire 181 is serrated to firmly grip the body 201 of the anchor 186.

As shown in FIG. 29, the clam shell member 187 includes a series of longitudinally spaced holes 203 which receive the pivot pins 202 of the anchors 186 at the proximal ends of the wires 181. Similarly, the mating clam shell section 188 includes a series of longitudinally spaced holes 204 for receiving the pivot pins 202 of the anchors 186 at the proximal ends of the wires 181.

As shown FIG. 28, the elongated proximal clam shell member 187 includes a series of longitudinally spaced fastener posts 205 which are adapted to be snap fit into a corresponding set of bores 206 formed in the mating clam shell section 188. Each fastener post 205 includes an outwardly projecting annular lip 207 at its free end for engaging an annular groove 208 (FIG. 27) in each bore 206 to provide the snap fit of the fastener post 205 into the bore 206. Each fastener post 205 includes an enlarged pedestal 209 which serves as a spacer to maintain a sufficient space between the elongated proximal clam shell member 187 and the mating clam shell section 188 to receive the anchors 186 therebetween. The elongated clam shell member 187 also includes a longitudinal bore 210 formed in its semi-cylindrical extension 189 for receiving the actuator rod 175 which is connected to one of the actuator slides 200. The upper and lower platforms 180 are substantially identical in construction and are independently operable by the actuator slides 200 at the top and bottom of the handle assembly 160.

Preferably, except for the wires 181, the other frame components including the anchors 182 and 186, the distal clam shell members 183 and 184, and the proximal clam shell member 187 and its mating clam shell section 188 are made of plastic material. The support tube 170 and actuator rod 175 consist of stainless steel. The components of the handle assembly 160 and the actuator slides 200 are made of plastic material.

Referring to FIGS. 12-14, the actuator slides 200 of the double-sided tissue manipulator 150 are substantially identical in construction to the actuator slide 110 (FIG. 6) described above. Each actuator slide 200 has a narrow elongated neck 212 which is slidably received in one of the slots 162 in the handle assembly 160. The neck 212 is connected to the front of an elongated base 214 which is slidably supported by a horizontal partition 165 extending along the longitudinal axis of the handle assembly 160. The proximal end of the actuator rod 175 is also connected to the front of the base 214. A resilient hinge 216 is mounted at the rear of the base 214 and is provided with a set of pawls 218 which are normally biased by the resilient hinge 216 into engagement with a ratchet 220 on the inside of each of the handle sections 163 and 164 to retain the actuator slide 200 in a selected position on the handle assembly 160. The pawls 218 and the ratchets 220 provide a ratchet mechanism for retaining the frame members or wires 181 in an outwardly expanded configuration or an inwardly collapsed configuration. A manually operable release button 222 extends upwardly from the resilient hinge 216 through an opening in the actuator slide 200. A release button 222 is depressed to disengage the pawls 218 from the ratchet 220 to allow the frame members 181 to return to the collapsed configuration. As the release button 222 is depressed, the thumb of the surgeon also engages the actuator slide 200 to prevent the sudden collapse of the frame members 181 when the pawls 218 are disengaged from the ratchet.

In the operation of the double-sided tissue manipulator 150 of FIGS. 11-15, the two actuator slides 200 allow the surgeon to selectively expand one or both of the expandable frames 180. As shown in FIG. 12, one of the tissue manipulating frames 180 can be expanded, while the other frame remains collapsed. Also, referring to FIG. 13, one of the frames 180 can be fully expanded, while the other frame is only partially expanded. Further, as shown in FIG. 14, both frames 180 can be fully expanded. The frames 180 provide substantially planar platforms which are located in the same plane with the longitudinal axis of the support tube 170. The double-sided tissue manipulator 150 is used to manipulate tissue in substantially the same manner as the single-sided tissue manipulator 50 previously described.

The invention in its broader aspects is not limited to the specific details of the preferred embodiments shown and described, and those skilled in the art will recognize that the invention can be practiced with modification within the spirit and scope of the appended claims.

We claim:

1. An endoscopic tissue manipulator, comprising:
a handle;
a support tube extending from said handle and defining a longitudinal axis, said support tube including an elongated continuous slot formed therein, said slot having a plane normal to said longitudinal axis;
an expandable frame mounted within said support tube adjacent to said slot; and
means for expanding said frame transversely from said support tube through said slot to provide a spatula-shaped in an expanded configuration platform for manipulating tissue;
wherein said frame comprises a plurality of elongated flexible frame members, each frame member being adapted to flex laterally to extend through said slot, in a common transverse direction relative to said support tube.

2. The tissue manipulator of claim 1 wherein:
each frame member is adapted to bend into a bow-shaped configuration extending from said slot and so that each said frame member overlaps at least one of the other frame members of said platform.

3. The tissue manipulator of claim 2, wherein:
said spatula-shaped platform is substantially planar platform located in the same plane with the longitudinal axis of said support tube.

4. The tissue manipulator of claim 2, which includes:
means for retaining said frame in the expanded configuration.

5. The tissue manipulator of claim 1, wherein said frame members plurality of frame members comprises a series of wires adapted to expand laterally outward from said support tube.

6. An endoscopic tissue manipulator, comprising:
a handle;
a support tube extending from said handle and including an elongated slot formed therein;
an expandable frame mounted within said support tube adjacent to said slot; and
means for expanding said frame transversely from said support tube through said slot to provide a spatula-shaped platform for manipulating tissue;
wherein said frame comprises a plurality of elongated flexible frame members, each frame member being adapted to flex laterally relative to said support tube;
wherein said plurality of frame members comprises a series of wires adapted to expand laterally outward from said support tube; and
wherein said wires are staggered along said support tube and arranged in an overlapping relationship with respect to one another.

7. An endoscopic tissue manipulator, comprising:
a handle;
a support tube extending from said handle and defining a longitudinal axis, said support rube including a pair of elongated slots formed therein on opposite sides, relative to any plane normal to the longitudinal axis which is not common to any one of said pair of said slots, of said support tube, each of said pair of elongated slots having a plane normal to said longitudinal axis;

a pair of expandable frames mounted within said support tube each of said expandable frames being located adjacent to one of said slots; and means for selectively expanding said frames transversely from said support tube through said slots to provide a pair of spatula-shaped platforms for manipulating tissue;

wherein each of said pair of frames comprises a plurality of elongated flexible frame members, each frame member being adapted to flex laterally relative to said support tube.

8. The tissue manipulator of claim 7, wherein said plurality of frame members comprises:

a series of wires adapted to expand laterally outward from said support tube into a substantially planar configuration to form said pair of spatula-shaped platforms for manipulating the tissue.

9. An endoscopic tissue manipulator, comprising:

a handle;

a support tube extending from said handle and including a pair of elongated slots therein on opposite sides of said support tube;

a pair of expandable frames mounted within said support tube each of said expandable frames being located adjacent to one of said slots; and means for selectively expanding said frames transversely from said support tube through said slots to provide a pair of spatula-shaped platforms in expanded configurations for manipulating tissue;

wherein each of said pair of frames comprises a plurality of elongated flexible frame members, each frame member being adapted to flex laterally relative to said support tube; and wherein each frame member is adapted to bend into a bow-shaped configuration extending from one of said slots and so that each frame member overlaps at least one of the other frame members of one of the platforms.

10. The tissue manipulator of claim 9, wherein;

each said spatula-shape platform is substantially planar platform located in the same plane with the longitudinal axis of said support tube.

11. The tissue manipulator of claim 9, which includes:

means for retaining said frame members of each platform in the expanded configuration.

12. An endoscopic tissue manipulator, comprising:

a handle;

a support tube extending from said handle and including a pair of elongated slots formed therein on opposite sides of said support tube;

a pair of expandable frames mounted within said support tube each of said expandable frames being located adjacent to one of said slots; and means for selectively expanding said frames transversely from said support tube through said slots to provide a pair of spatula-shaped platforms for manipulating tissue;

wherein each of said pair of frames comprises a plurality of elongated flexible frame members, each frame member being adapted to flex laterally relative to said support tube;

wherein said plurality of frame members comprises a series of wires adapted to expand laterally outward from said support tube; and wherein said wires are staggered along said support tube and arranged in an overlapping relationship with respect to one another.

13. An endoscopic tissue manipulator, comprising:

a handle;

an elongated hollow support tube extending from said handle and defining a longitudinal axis, said tube having a longitudinal continuous slot formed therein adjacent to its distal end, said slot having a plane normal to said longitudinal axis;

an actuator member mounted for longitudinal movement relative to said support tube;

an expandable frame comprising a plurality of elongated flexible frame members, each of said frame members being connected at its opposite ends to said support tube and to said actuator member; and said frame members being adapted to flex in a common direction transverse relative to said longitudinal axis through said slot in said support tube by movement of said actuator member relative to said support tube to provide a spatula-shaped platform in an expanded configuration for manipulating tissue.

14. The tissue manipulator of claim 13, wherein:

said frame members are adapted to expand from a collapsed configuration within said support tube to the expanded configuration, wherein said frame members project laterally from said slot in said support tube.

15. The tissue manipulator of claim 14, which includes:

a manually operable actuator slide mounted on said handle and connected to said actuator member for moving said actuator member relative to said support tube to expand and collapse said frame members.

16. The tissue manipulator of claim 15, which includes:

ratchet means on said handle for releaseably engaging said actuator slide to retain said frame members in said expanded and said collapsed configuration.

17. The tissue manipulator of claim 16, which includes:

a manually operable release button on said actuator slide for disengaging said actuator slide from said ratchet means to allow said frame members to move between the expanded configuration and the collapsed configuration.

18. An endoscopic tissue manipulator, comprising:

a handle;

an elongated hollow support tube extending from said handle and defining a longitudinal axis, said tube having a longitudinal slot formed therein adjacent to its distal end;

an actuator member mounted for longitudinal movement relative to said support tube;

an expandable frame comprising a plurality of elongated flexible frame members, each of said frame members being connected at its opposite ends to said support tube and to said actuator member; and said frame members being adapted to flex transversely relative to said longitudinal axis through said slot in said support tube by movement of said actuator member relative to said support tube to provide a spatula-shaped platform in an expanded configuration for manipulating tissue;

wherein each frame member is adapted to bend into a bow-shaped configuration extending laterally from said slot and so that each said frame member overlaps at least one of the other frame members of said platform.

19. The tissue manipulator of claim 18, wherein said plurality frame members comprises:
a series of wires adapted to expand laterally outward from a collapsed configuration within said support tube into the expanded configuration which is substantially planar.

20. The tissue manipulator of claim 19, wherein:
said wires are staggered along said support tube and arranged in an overlapping relationship with respect to one another.

21. The tissue manipulator of claim 20, which includes:
means for pivotally connecting a distal end of each wire to said support tube.

22. The tissue manipulator of claim 21, which includes:
means for pivotally connecting a proximal end of each wire to said actuator member.

23. An endoscopic tissue manipulator, comprising:
a handle;
an elongated hollow support tube extending from said handle and defining a longitudinal axis, said support tube having a pair of longitudinal slots formed on opposite sides thereof adjacent to its distal end;
a pair of actuator members mounted for longitudinal movement relative to said support tube;
a pair of expandable frames each comprising a set of elongated flexible frame members, each set of frame members being connected at its opposite ends to said support tube and to one of said actuator members; and
each set of frame members being adapted to flex transversely relative to said longitudinal axis through one of said slots by movement of one of said actuator members relative to said support tube to provide a pair of spatula-shaped platforms in expanded configurations for manipulating tissue.

24. The tissue manipulator of claim 23, wherein:
each frame member is adapted to bend into a bow-shaped configuration extending laterally from one of said slots and overlapping the other frame members of one of the platforms.

25. The tissue manipulator of claim 24, wherein each set of frame members comprises:
a series of wires adapted to expand laterally outward from a collapsed configuration within said support tube into the expanded configuration which is substantially planar.

26. The tissue manipulator of claim 25, wherein:
said wires are staggered along said support tube and arranged in an overlapping relationship with respect to one another.

27. The tissue manipulator of claim 26, which includes:
means for pivotally connecting a distal end of each wire to said support tube.

28. The tissue manipulator of claim 27, which includes:
means for pivotally connecting a proximal end of each wire to one of said actuator members.

29. The tissue manipulator of claim 23, wherein:
each set of frame members is adapted to expand from a collapsed configuration within said support tube to the expanded configuration projecting laterally from said slot in said support tube.

30. The tissue manipulator of claim 29, which includes:
a pair of manually operable actuator slides mounted on said handle, each slide being connected to one of said actuator members for moving said actuator member relative to said support tube to expand and collapse one set of said frame members.

31. The tissue manipulator of claim 30, which includes:
ratchet means on said handle for releaseably engaging each of said actuator slides to retain each set of said frame members in said expanded and said collapsed configuration.

32. The tissue manipulator of claim 31, which includes:
a manually operable release button on each actuator slide for disengaging said actuator slide from said ratchet means to allow each set of frame members to move between the expanded configuration and the collapsed configuration.

* * * * *

UNITED STATES PATENT AND TRADEMARK OFFICE
CERTIFICATE OF CORRECTION

PATENT NO. : 5,325,848
DATED : July 5, 1994
INVENTOR(S) : Ronald D. Adams, Randy J. Embertson, M. Joshua Tolkoff, Robert C. Allman, and Fernando A. de Toledo It is certified that error appears in the above-indentified patent and that said Letters Patent is hereby corrected as shown below:

Claim 1, column 12, line 19 "platform" should be inserted after "spatula-shaped", after "configuration" delete "plat-form".

Claim 3, column 12, line 33 "adapted to form a" should be inserted after "is".

Claim 5, column 12, line 39 after "said" delete "frame members".

Claim 10, column 13, line 43 "adapted to form a" should be inserted after "is".

Claim 29, column 16, line 24 delete "projecting" and insert "wherein said frame members project".

Signed and Sealed this

Sixteenth Day of July, 1996

Attest:

BRUCE LEHMAN

*Attesting Officer*  *Commissioner of Patents and Trademarks*